United States Patent [19]
Kurek et al.

[11] Patent Number: 5,214,211
[45] Date of Patent: May 25, 1993

[54] ALKYLATION OF DIARYLAMINES WITH OLEFINS USING RARE EARTH MODIFIED PILLARED CLAYS

[75] Inventors: Paul R. Kurek, Barrington; Jennifer S. Holmgren, Bloomingdale, both of Ill.

[73] Assignee: UOP, Des Plaines, Ill.

[21] Appl. No.: 805,747

[22] Filed: Dec. 12, 1991

[51] Int. Cl.$^5$ ............................................ C07C 209/60
[52] U.S. Cl. ...................................... 564/409; 502/68
[58] Field of Search .................... 564/409; 502/65, 68, 502/84

[56] References Cited

U.S. PATENT DOCUMENTS

| | | | |
|---|---|---|---|
| 4,163,757 | 8/1979 | D'Sidocky | 260/570 R |
| 4,952,544 | 8/1990 | McCauley | 502/68 |
| 4,957,889 | 9/1990 | McCauley | 502/65 |

FOREIGN PATENT DOCUMENTS 1051271  2/1959  Fed. Rep. of Germany.

Primary Examiner—Glennon H. Hollrah
Assistant Examiner—Brian M. Burn
Attorney, Agent, or Firm—Thomas K. McBride; Eugene I. Snyder

[57] ABSTRACT

Rare earth pillared clays, and especially cerium and lanthanum aluminum chlorohydrite pillared clays, are quite effective catalysts in the alkylation of diaryl amines at temperatures in the range of 100°–225° C. The catalysts effect alkylation using olefins as the alkylating agent with high conversion and with minimal cracking of either the olefin or the alkylated product. Catalysts may be regenerated by heating in air at temperatures of at least about 550°–600° C. Water in small amounts also modifies the reaction to further reduce cracking although it also reduces the activity of the catalyst.

23 Claims, No Drawings

ALKYLATION OF DIARYLAMINES WITH OLEFINS USING RARE EARTH MODIFIED PILLARED CLAYS

BACKGROUND OF THE INVENTION

The alkylation of an aromatic ring by alkyl halides, alcohols, and olefins is an extremely useful and important reaction. Commercial processes are replete with examples of aromatic alkylation to afford a diversity of products. Where the aromatic ring being alkylated is that of a diarylamine, the alkylation products, and especially the dialkylated diarylamine-i.e., the product where each aryl moiety of a diarylamine is monoalkylated-find substantial use in, for example, automotive products such as transmission fluids and power steering oils. The traditional catalyst employed for the latter alkylations are for the most part traditional Friedel Crafts catalysts such as aluminum chloride, boron trifluoride, and so forth. However, other catalysts, and in particular solid catalysts such as zeolites, synthetic molecular sieves, and silica-alumina, have been extensively employed as alkylation catalysts, especially where a bed of solid catalyst is desired to be utilized in a continuous alkylation process.

As is often the case there is not just a single reaction occurring during the alkylation of a diarylamine by an olefin, but instead one finds several concurrent reactions which tend to afford undesirable byproducts, to lower the conversion of the diarylamine to the sought-for products, to consume olefin unproductively, and often to substantially complicate the isolation of the desired reaction products because of the increased complexity of the reaction product mixture. More particularly, with olefins as alkylating agents alkylation catalysts also cause oligomerization of the olefins, cracking of the olefins, and cracking of the alkyl moiety of the alkylated diarylamine, all of which are acid catalyzed reactions. This can be illustrated using diisobutylene as the representative olefin and diphenylamine as the representative diarylamine.

A good selectively to dialkylated product is important where the latter is the product sought, and a high selectivity to retaining the carbon number of the olefin means that one is avoiding the formation of products other than what is sought. Finally, minimization of oligomerization and cracking of the olefins means minimizing olefin loss.

The family of catalysts which we have identified that satisfy all of the above criteria are pillared clays whose pillars have been modified by incorporation of rare earth salts. More specifically, the catalysts are clays intercalated with pillars of oligomeric oxycations of aluminum, zirconium, or chromium which are complexed with or otherwise incorporate rare earth cations. These materials are described in great detail in U.S. Pat. Nos. 4,952,544 and 4,957,889, both of which are hereby incorporated by reference. For convenience, this class of materials subsequently will be referred to within as rare earth pillared clays and will be described more fully within.

SUMMARY OF THE INVENTION

The purpose of this invention is to alkylate diarylamines with olefins at high conversions of the diarylamine and with minimal cracking and oligomerization of the olefin along with minimal cracking of the alkyl group(s) of the alkylated diarylamine. One embodiment comprises reacting the diarylamine with an olefin in the presence of a rare earth pillared clay. In a more specific embodiment the amine is diphenylamine. In yet a more specific embodiment the diphenylamine is alkylated by diisobutylene. In yet another embodiment the rare earth pillared clay is an aluminum chlorohydrate pillared clay which has been modified by at least one cerium or lanthanum salt. Other embodiments will become apparent from the ensuing description.

DESCRIPTION OF THE INVENTION

In testing various materials as catalysts for the alkylation of diarylamines we have found that rare earth pillared clays are unique in satisfying the catalytic criteria

| | |
|---|---|
| Diisobutylene→ 2 isobutylene | CRACKING |
| Diisobutylene→ dimers, trimers, etc. | OLIGOMERIZATION |
| $(C_6H_5)_2N$ + diisobutylene→ $C_8H_{17}$—$C_6H_4$—NH—$C_6H_4$—$C_8H_{17}$ | ALKYLATION |
| $C_8H_{17}$—$C_6H_4$—N—$C_6H_4$—$C_8H_{17}$→ $C_8H_{17}$—$C_6H_4$—N—$C_6H_4$—$C_4H_9$ + isobutylene | CRACKING |

Our interest was to identify a solid catalyst usable in a fixed bed continuous process which would effect the alkylation of diarylamines by olefins: 1) at temperatures no greater than 225° C; 2) with high (at least 95%) conversion of the diarylamine; 3) at an olefin to diarylamine ratio of no more than 10:1; 4) with good selectivity to the dialkylated product; 5) with excellent (>90%) selectivity to alkylated products where the alkyl group has the same carbon numbers as the olefin, and; 6) with minimal oligomerization and cracking of the olefin. An additional critical requirement is that the catalyst must be regenerable. Each of the foregoing conditions can be examined individually for its benefits. Lower temperatures are desirable not only to minimize energy costs but also to minimize thermal reactions which generally are degradative. A high conversion of the diarylamine is synonymous with its efficient utilization, so long as the conversion is attended by high selectivity to the desired products. A lower olefin to diarylamine ratios means that less olefin needs to be recycled and therefore smaller reactors are needed for any given productivity.

articulated above. Thus, although these materials are more expensive than many other putative catalysts, their unique combination of properties makes them exceptionally well suited for use as catalysts in the aforementioned process. Nothing in the prior art leads one to expect that rare earth pillared clays manifest such singularity in the properties required for alkylation of diarylamines. The process we have developed is one where diarylamines are alkylated by olefins in a temperature domain of 100°-225° C. in the presence of a rare earth pillared clay as the catalyst to effect at least 95% conversion of the diarylamine while effecting negligible oligomerization and negligible cracking of either the olefin or of the alkylated products.

The reactants to be alkylated are diarylamines of the formula $Ar_2NH$, where Ar is an aromatic ring. In the most usual case Ar is the phenyl group, but other monovalent radicals of aromatic hydrocarbons also may be used in the practice of this invention. Exemplary of the latter are naphthyl, anthracenyl, phenanthryl, chrysenyl, biphenylyl, and so forth. One or both of the aromatic rings in the diarylamines also may bear at least one substituent such as a halogen, especially fluorine, chlorine, and bromine, an alkyl, an alkoxy, or a carboalkoxy group (i.e., an ester) where the alkyl portion contains from 1 through 20 carbon atoms, and the hydroxyl moiety. As the number of groups on any one aryl ring increases, alkylation according to the invention described herein may become increasingly difficult, especially because of steric effects. Consequently the diphenylamine contains no more than one substituent in each ring in the most usual case.

Alkylation of the diarylamines of this invention is effected using an olefin in the presence of a rare earth pillared clay as catalyst. The olefins which are most often used contain between about 4 and about 20 carbon atoms, but those containing from 6 through about 14 carbon atoms are particularly favored. Among the olefins which may be employed are the isomeric butenes (i.e., butene-1, butene-2, methylpropane-1, otherwise known as isobutylene) and the isomeric pentenes, hexenes, heptanes, octenes, nonenes, decenes, undecenes, dodecenes, tridecenes, tetradecenes, pentadecenes, hexadecenes, heptadecenes, octadecenes, nonadecenes, and the isomeric eicosenes. Of particular interest are the propylene and isobutylene oligomers, especially the $C_8$ olefin diisobutylene, which is prepared as a dimer of isobutylene.

Pillared clays are generally referred to by the acronym PILC, and the catalysts of this invention are rare earth PILCs. Rare earth PILCs are a 2:1 layered clay intercalated with a cationic oxyoligomer of chromium, zirconium, or aluminum which is complexed with or which otherwise incorporates one or more rare earth cations, generally in the trivalent state. Such materials are improved over PILCs which lack the rare earth cation because they have significantly higher hydrothermal stability as reflected by their higher surface areas and their stability to steaming in the 750°–800° C. range. In contrast, in the absence of the rare earth cations pillars generally collapse at 650° C. or less.

The clays useful in our invention are crystalline, expandable, colloidal clays or clay minerals of the 3-layer type, i.e., sheet structures composed of two layers of silica tetrahedra and one central dioctahedral or trioctahedral layer, and can be either natural or synthetic. Smectites are 2:1 layered clay minerals that carry a lattice charge and characteristically expand when solvated with water and alcohol. Examples of suitable smectites include montmorillonite, bentonite, beidellite, hectorite, saponite, sauconite, nontronite, and analogs thereof. Both dioctahedral and trioctahedral smectities can be used. The clays are usually in the alkali metal form such as sodium montmorillonite, the sodium form being preferred. However, the clays can be in other metal forms, such as calcium, other alkaline earth metals, alkali metals, cerium, nickel, iron, chromium, beryllium, titanium, and boron. The preferred smectite clays have a negative layer charge of about 0.5 to 1 per silica tetrahedra.

The pillars are rare earth modified oligomeric oxycations of aluminum, chromium, or zirconium which arise from polymeric cationic hydroxyl inorganic metal complexes of aluminum, chromium, or zirconium in conjunction with a rare earth salt, and generally a water soluble rare earth salt. The preferred polymeric cationic hydroxyl inorganic metal complexes are basic aluminum complexes formed by the hydrolysis of aluminum salts, basic zirconium complexes formed by the hydrolysis of zirconium salts, and basic chromium complexes formed by the hydrolysis of chromium salts. Highly preferred polymeric cationic hydroxyl inorganic metal complexes are the basic aluminum complexes, and the most preferred basic aluminum complex is the chlorohydrate. The basic aluminum, zirconium and chromium complexes can be used either alone or in combination. PILCs whose pillars arise from aluminum chlorohydrate often are referred to as ACH PILCs. The class of inorganic complexes and polymers which may be used are more completely described in U.S. Pat. No. 4,952,544, which has been incorporated by reference.

As to the rare earth cation, at least one rare earth salt, generally water soluble, is incorporated in and modifies the polymeric cationic hydroxyl inorganic metal complex which is transformed, after heating and calcination, into the pillars which hold apart the clay layers to afford materials having an interlayer distance on the order of 17–25 Angstroms. Any suitable rare earth salt can be used, although water soluble rare earth salts are favored, with the most favored one being $Ce(NO_3)_3$. A preferred class of water soluble rare earth salts is that of the water soluble cerium salts, although the most preferred class consists of the water soluble lanthanum salts, and preferred soluble rare earth salts include $LaCl_3$ and $CeCl_3$. Because the rare earths usually occur in mixed form and are expensive to separate, generally mixtures of rare earth salts are most likely to be used.

The rare earth elements are those with atomic numbers 57 through 71, plus yttrium and scandium. The recommended rare earth salts are those which are trivalent, although rare earth salts having other oxidation states also may be useful. The weight ratio of the rare earth to aluminum, zirconium, or chromium in the polymerized solution of the latter, as measured by the weight ratio of the elements as their oxide, typically ranges from 1:52 to 1:1, but appears to be without any effect on the product because excess of the rare earth salt is lost during washing of the finished product. The most preferred rare earth pillared clays of this invention are those containing cerium- and lanthanum-modified aluminum chlorohydrate pillars and are referred to as CeACH PILC or LaACH PILC respectively.

The rare earth PILCs of this invention are particularly desirable because of the stabilization of the pillars toward thermal degradation, which is an important feature with respect to the regeneration of deactivated catalysts. We have observed that highly colored materials, speculated to be either carbazole or acridine dyes, bind strongly to the alkylation catalyst and rapidly deactivate it. Regeneration generally requires heating in air at a temperature at least in the 550°–600° C. range. It is then clear that if a regenerable catalyst is sought, the catalyst must be structurally stable upon repeated exposure to thermal treatment in oxygen at temperatures of at least 550°–600° C. Without incorporation of the rare earth salts the PILCs do not have the requisite thermal stability.

Alkylation usually is conducted within a temperature range from about 100° up to about 225° C. The exact temperature employed will depend upon the nature of the diarylamine, what olefin is being used as the alkylating agent, the liquid hourly space velocity sought, the susceptibility of the reactants and products to thermal degradation, and so forth. Reactions are conducted at pressures between atmospheric and about 3000 psig.

Where the reaction is performed at a pressure higher than the autogeneous pressure of the reaction mixture, an inert atmosphere is supplied, such as nitrogen, argon, hydrogen, and so forth. Where hydrogen is employed it may have the effect of improving product quality and extending catalyst life, and consequently is a somewhat preferred gas. However, although the gas chosen may have somewhat of an effect on the reaction, the choice of a particular gas to be used as an inert atmosphere is well within the scope of the person having ordinary skill in the art. The olefin generally is used in excess relative to the diarylamine, and molar proportions of olefin from about 2 to about 10 are most generally used, with a molar ratio of olefin: diarylamine between about 3:1 and 6:1 being most frequently employed.

Although the reaction may be run in a solvent, in the usual case no solvent will be employed. However, we have noticed that water has an important effect on the course of the reaction. In particular, we have found that if the reaction is done in the presence of water the latter has not only a slight deactivating effect on the reaction but, more importantly, it decreases even further the extent of cracking. Consequently, for optimum results effecting the reaction in the presence of water is recommended. Water is generally used at a concentration from about 0.1 up to about 10 weight percent based on the feed (i.e., reactant) mixture, although in appropriate circumstances the water concentration may be as high as 50 weight percent. Typically, concentrations in the range of 1-5% seem optimum. Other solvents also may have a similar effect, and such materials include alcohols, ketones, esters, ethers, cycloaliphatics, aromatics, and so forth.

Alkylation of a diarylamine with olefins in the presence of the rare earth PILCs of our invention may be carried out in either a batch or a continuous mode, with a continuous mode being highly favored. Where the reaction is performed continuously one may use a packed bed of the solid rare earth PILCs of this invention, although a radial bed, expanded bed, fluidized bed, and so forth also may be employed where desired. A particularly simple and desirable arrangement is one where the catalyst is used as a packed bed and the reactants are passed either upflow or downflow over the catalyst. Temperatures in the reaction zone may be from about 100° to about 225° C. with pressures in the range of atmospheric up to about 3000 psig being employed. The olefin typically will be used in a molar proportion relative to the diarylamine of between about 2 and about 10, most usually between about 3 and about 6. The liquid hourly space velocity is adjusted to afford the desired productivity, subject to the prerequisite that at least 95% of the diarylamine is reacted, and that preferably at least 97% is reacted. In a desirable variant a polar material, most notably water, is added to the feedstock to further minimize cracking which may accompany alkylation.

The following examples are only illustrative of our invention and even though they may be limited in exemplifying the invention it is not intended to limit the invention thereby in any means.

EXAMPLES 1-33

Preparation of the rare earth-ACH sol. A solution of 3.75 g of $LaCl_3.H_2O$ (purchased from Aldrich) and 65 g of aluminum chlorohydrol sol (purchased from Reheis) was placed in a Teflon lined 125 cc Parr Reactor. This solution was aged at 130°-140° C. for 3-5 days. The resulting rare earth-ACH sol was then used to pillar the montmorillonite clay.

Pillaring. A solution containing 35 g of the rare earth-ACH sol was mixed with 400 g of $H_2O$. This solution was stirred using a high shear mixer. While mixing, 35 g of montmorillonite clay (HPM-20, American Colloid) was added. This slurry was mixed for 30 minutes. After this time, the clay was recovered using a centrifuge and washed until the supernatant was substantially chloride free. The clay was then dried at 110° C. After grinding, the clay was calcined at 600° C. for a period of 3 hours.

Alkylation. To a glass-lined bomb was charged diphenylamine and diisobutylene in amounts given in the table. The indicated amount of catalyst was added, the bomb was placed in the autoclave, the autoclave was flushed with an inert gas, then charged to the indicated pressure and held at the temperatures and times in the table. The autoclave was allowed to cool, then vented and the catalyst removed by filtration. The filtrate was analyzed by GC to afford the results in the table.

Catalyst Regeneration. When the rare earth exchanged PILCs become noticeably deactivated they can be readily regenerated by what is essentially a carbon burn. Catalyst was heated up to about 600° C. over about 3 hours and maintained at that temperature in an air flow for a period varying with sample size, and normally 1-2 hours for small samples employed here.

Among others, the table clearly shows the relative inactivity of an ACH PILC which is not exchanged with a rare earth cation (Example 1), and the large increase in selectivity of rare earth exchanged ACH PILCs relative to aluminum cation exchanged clays (not PILCs). One also can readily discern the effect of water in reducing the amount of cracked products (BOD and MBD).

TABLE 1

Alkylation of Diphenylamine with Diisobutylene under Varying Conditions

| | | | SOLVENT | | | CATALYST | |
|---|---|---|---|---|---|---|---|
| EXAMPLE | $DPA^a$ | $DIB^b$ | AMT. | TYPE | $MR^c$ | TYPE | AMT |
| 1 | 0.12 | 0.65 | — | — | 5:1 | ACH PILC 80/20 $Al_2O_3^h$ | 5 g |
| 2 | 0.12 | 0.65 | — | — | 5:1 | $Al^{+3}$ $CLAY^k$ | 5 g |
| 3 | 0.12 | 0.65 | — | — | 5:1 | $Al^{+3}$ $CLAY^k$ | 5 g |
| 4 | 0.12 | 0.65 | 26 g | TOLUENE | 5:1 | $Al^{+3}$ $CLAY^k$ | 5 g |
| 5 | 0.12 | 0.65 | 2 g | WATER | 5:1 | $Al^{+3}$ $CLAY^k$ | 5 g |
| 6 | 0.15 | 0.65 | — | — | 5:1 | CeACH PILC | 5 g |
| 7 | 0.15 | 0.65 | — | — | 5:1 | CeACH PILC | 5 g |
| 8 | 0.15 | 0.65 | — | — | 5:1 | CeACH PILC | 5 g |
| 9 | 0.15 | 0.65 | — | — | 5:1 | CeACH PILC | 5 g |
| 10 | 0.15 | 0.65 | — | — | 5:1 | CeACH PILC | 5 g |
| 11 | 0.15 | 0.65 | — | — | 5:1 | CeACH PILC | 5 g |
| 12 | 0.15 | 0.65 | — | — | 5:1 | CeACH PILC | 5 g |
| 13 | 0.15 | 0.65 | 2 g | $H_2O$ | 5:1 | CeACH PILC | 5 g |
| 14 | 0.15 | 0.65 | 2 g | $H_2O$ | 5:1 | CeACH PILC | 5 g |

TABLE 1-continued

Alkylation of Diphenylamine with Diisobutylene under Varying Conditions

| Example | a | b | additive amt | additive | ratio c | catalyst | cat amt | Time HRS | Temp | P, gas[d] | Conv[e] DPA | MBD | MOD | BOD | DOD |
|---|---|---|---|---|---|---|---|---|---|---|---|---|---|---|---|
| 15 | 0.15 | 0.65 | 2 g | H$_2$O | 5:1 | CeACH PILC | 5 g | 1 | 180 | 1000 PSIG H$_2$ | 98 | 0 | 26 | 2 | 66 |
| 16 | 0.15 | 0.65 | 2 g | H$_2$O | 5:1 | CeACH PILC | 5 g | 1 | 180 | 1000 PSIG H$_2$ | 98 | 0 | 27 | 1 | 66 |
| 17 | 0.15 | 0.65 | 2 g | H$_2$O | 5:1 | CeACH PILC | 5 g | 1 | 180 | 1000 PSIG H$_2$ | 98 | 0 | 27 | 2 | 64 |
| 18 | 0.12 | 0.65 | — | — | 5:1 | CeACH PILC[g] | 5 g | 8 | 180 | 1500 PSIG H$_2$ | 99 | 1 | 22 | 6 | 64 |
| 19 | 0.12 | 0.65 | — | — | 5:1 | CeACH PILC[g] | 5 g | 8 | 180 | 1500 PSIG H$_2$ | 95 | 0 | 35 | 1 | 56 |
| 20 | 0.24 | 0.73 | 150 g | DECALIN | 3:1 | CeACH PILC[g] | 5 g | 18 | 150 | 760 mm Hg N$_2$ | 92 | 0 | 48 | 0 | 49 |
| 21 | 0.15 | 0.52 | 1.7 g | WATER 2% | 3.5:1 | CeACH PILC | 5 g | 4 | 180 | 1500 PSIG H$_2$ | 95 | 4 | 38 | 6 | 49 |
| 22 | 0.12 | 0.65 | 1% | H$_2$O | 5:1 | CeACH PILC[h] | 5 g | 8 | 180 | 1500 PSIG N$_2$ | 98 | 0 | 26 | 2 | 66 |
| 23 | 0.12 | 0.65 | 1% | H$_2$O | 5:1 | CeACH PILC | 5 g | 8 | 180 | 1500 PSIG N$_2$ | 98 | 0 | 27 | 2 | 65 |
| 24 | 0.12 | 0.65 | — | — | 5:1 | CeACH PILC | 5 g | 8 | 180 | 1500 PSIG N$_2$ | 99 | 0 | 23 | 3 | 67 |
| 25 | 0.12 | 0.65 | 2 g | H$_2$O | 5:1 | CeACH PILC | 5 g | 8 | 180 | 1500 PSIG N$_2$ | 98 | 0 | 25 | 1 | 69 |
| 26 | 0.12 | 0.65 | 2 g | IPA | 5:1 | CeACH PILC | 5 g | 8 | 180 | 1500 PSIG N$_2$ | 97 | 0 | 28 | 1 | 64 |
| 27 | 0.25 | 1.25 | — | — | 5:1 | CeACH PILC | 5 g | 10 | 100-15 | 760 mm Hg N$_2$ | 87 | 1 | 45 | 1 | 47 |
| 28 | 0.12 | 0.65 | — | — | 5:1 | CeACH PILC[i] | 5 g | 8 | 180 | 1500 PSIG N$_2$ | 87 | 0 | 53 | 1 | 44 |
| 29 | 0.12 | 0.65 | — | — | 5:1 | LaACH PILC[g] | 5 g | 8 | 180 | 1500 PSIG N$_2$ | 98 | 1 | 24 | 5 | 64 |
| 30 | 0.12 | 0.65 | 2 g | H$_2$O | 5:1 | LaACH PILC | 5 g | 8 | 180 | 1500 PSIG N$_2$ | 99 | 0 | 23 | 3 | 70 |
| 31 | 0.12 | 0.65 | 2 g | WATER | 5:1 | LaACH PILC[j] | 5 g | 8 | 180 | 1500 PSIG N$_2$ | 89 | 0 | 56 | 1 | 41 |
| 32 | 0.12 | 0.65 | — | — | 5:1 | LaACH PILC[i] | 5 g | 8 | 180 | 1500 PSIG N$_2$ | 99 | 1 | 23 | 6 | 63 |
| 33 | 0.12 | 0.65 | — | — | 5:1 | LaACH PILC | 5 g | 8 | 180 | 1500 PSIG N$_2$ | 99 | 2 | 20 | 12 | 59 |

Note: Examples 1–14 shown on previous page. Per footnote, conversions and selectivities for examples 1–14 (from earlier portion of table) were:

| Example | Time HRS | Temp | P, gas[d] | Conv[e] DPA | MBD | MOD | BOD | DOD |
|---|---|---|---|---|---|---|---|---|
| 1 | 8 | 180 | 1500 PSIG N$_2$ | 7 | 11 | 73 | 3 | 11 |
| 2 | 8 | 180 | 1500 PSIG N$_2$ | 99 | 7 | 28 | 19 | 38 |
| 3 | 8 | 180 | 1500 PSIG N$_2$ | 99 | 3 | 23 | 15 | 48 |
| 4 | 8 | 180 | 1500 PSIG N$_2$ | 98 | 13 | 31 | 28 | 17 |
| 5 | 8 | 180 | 1500 PSIG N$_2$ | 98 | 13 | 30 | 30 | 20 |
| 6 | 1 | 180 | 1000 PSIG H$_2$ | 98 | 1 | 25 | 7 | 60 |
| 7 | 1 | 180 | 1000 PSIG H$_2$ | 98 | 1 | 25 | 5 | 61 |
| 8 | 1 | 180 | 1000 PSIG H$_2$ | 98 | 0 | 26 | 2 | 65 |
| 9 | 1 | 180 | 1000 PSIG H$_2$ | 98 | 0 | 24 | 3 | 63 |
| 10 | 1 | 180 | 1000 PSIG H$_2$ | 84 | 0 | 51 | 1 | 45 |
| 11 | 1 | 180 | 1000 PSIG H$_2$ | 98 | 0 | 26 | 1 | 64 |
| 12 | 1 | 180 | 1000 PSIG H$_2$ | 98 | 1 | 27 | 4 | 65 |
| 13 | 1 | 180 | 1000 PSIG H$_2$ | 92 | 0 | 41 | 1 | 55 |
| 14 | 1 | 180 | 1000 PSIG H$_2$ | 96 | 0 | 32 | 1 | 62 |

[a] Moles diphenylamine
[b] Moles diisobutylene
[c] Molar ratio diisobutylene:diphenylamine
[d] Pressure, inert gas
[e] Percent diphenylamine reacted
[f] Selectivity of products formed.
MBD = monobutyldiphenylamine; MOD = monooctyldiphenylamine; BOD = butyloctyldiphenylamine; DOD = dioctyldiphenylamine.
[g] Regenerated material; see description.
[h] Extrudate (other samples were as a powder).
[i] Recycled (i.e., reused) from a previous run.
[j] Recycled and regenerated.
[k] Clay impregnated with Al$^{+3}$ cations.

EXAMPLE 34

Continuous preparation of dioctyldiphenylamine. A hot molten feed stream of diphenylamine (DPA) may be passed through a guard bed (see below) to remove any contaminants or precursors to the formation of dyes. This stream may be joined with another stream containing diisobutylene (DIB). These streams may be pumped down flow into a fixed bed jacketed reactor so that the resulting composition of the feed stream contains a 5:1 mole ratio of DIB:DPA. The reaction may be conducted over a catalyst at 1 WHSV (100 g catalyst), using 1000 psig of inert gas (hydrogen, argon, helium, carbon monoxide or nitrogen). Nitrogen may be preferred due to cost and inflammability.

The catalyst can be an extrudated rare earth metal PILC such as La or CeACH PILC (note that the form of the catalyst can be spherical, pellet or crushed irregular shape). A catalyst activation procedure could be employed prior to start up of the feeds. The procedure would be to heat the catalyst to between 500°–600° C. in nitrogen or air for 1 hour. The catalyst bed would be cooled and the feeds cut in.

A line out period of 4 hours could be given to balance the feed rates. Temperature would be maintained to give proper selectivity and conversions. The temperature of the catalyst hot spot could be maintained between 100°–225° C. depending upon the WHSV, desired product distribution, and so forth.

The product produced in the main reactor can then be sent to a crystallizer and cooled to form crystals of DOD in 85% yield. The product can be rinsed with cyclohexane, isooctane or other insoluble solvent to give DOD with 99% purity. The solvent wash would be taken off as a separate stream while the initial filtrate containing unreacted DPA and MOD can be recycled. Optionally a fractional distillation can be performed to recover DOD as a bottoms product and recycle the distillate containing DPA, MOD and DIB. A side stream may be required to remove MBD, BOD, (by-products) and polymers of DIB if they become concentrated so as to interfere with the process.

Pretreatment of feeds. In fixed bed reactions it may be advantageous to pretreat the feed to remove dye precursors which deactivate the catalyst. To pretreat the feed, a guard bed may be used. This is a smaller reactor that is ahead of the main reactor and is filled with a clay or alumina and DPA passed through it. The treated DPA is then combined with DIB prior to entry into the main reactor where the alkylation takes place.

What is claimed is:

1. A process for alkylating a diarylamine with an olefin whereby at least 95% of the diarylamine is reacted comprising reacting under alkylation conditions the diarylamine with from 2 to about 10 molar proportions of an olefin containing from 4 through 20 carbon atoms in the presence of a clay intercalated with pillars of oligomeric oxycations of aluminum, zirconium, or chromium as modified by rare earth salts.

2. The process of claim 1 where alkylation conditions include a temperature between about 100° and 225° C. and a pressure between about atmospheric and 3000 psig.

3. The process of claim 1 where the diarylamine is diphenylamine.

4. The process of claim 1 where the diarylamine is a diphenylamine having at least one substituent on at least one of the aromatic rings, said substituent being selected from the group consisting of fluorine, chlorine, bromine, an alkyl, an alkoxy, or a carboalkoxy moiety having from 1 to 20 carbons, or an hydroxy moiety.

5. The process of claim 1 where the olefin contains from 6 through about 14 carbon atoms.

6. The process of claim 1 where the olefin is a propylene or isobutylene oligomer.

7. The process of claim 6 where the olefin is diisobutylene.

8. The process of claim 1 where the diarylamine is reacted with from about 3 to about 6 molar proportions of olefin.

9. The process of claim 1 where the diarylamine is diphenylamine and the olefin is diisobutylene present in between 2.5 and 5 molar proportions.

10. The process of claim 1 where the clay has pillars of oligomeric oxycations of aluminum.

11. The process of claim 1 where the clay has pillars of oligomeric oxycations of chromium.

12. The process of claim 1 where the clay has pillars of oligomeric oxycations of zirconium.

13. The process of claim 10 where the clay has pillars arising from aluminum chlorohydrate.

14. The process of claim 1 where the rare earth salt is a salt of cerium.

15. The process of claim 1 where the rare earth salt is a salt of lanthanum.

16. The process of claim 1 where the clay has pillars arising from aluminum chlorohydrate as modified by cerium salts.

17. The process of claim 1 where the clay has pillars arising from aluminum chlorohydrate as modified by lanthanum salts.

18. The process of claim 1 where the diarylamine is diphenylamine, the olefin is diisobutylene, and the clay has pillars arising from aluminum chlorohydrate as modified by at least one of a cerium or lanthanum salt.

19. The process of claim 1 further characterized in that the reaction is conducted in the presence of water at a concentration, relative to the feeds, of from about 0.1 to about 50 weight percent.

20. The process of claim 19 where water is present at a concentration from about 0.1 up to about 10 weight percent.

21. The process of claim 20 where water is present at a concentration from about 1 up to about 5 weight percent.

22. The process of claim 1 where at least 97% of the diarylamine is reacted.

23. The process of claim 1 further characterized in that the reaction is performed in a hydrogen atmosphere.

* * * * *